(12) United States Patent
Kitic

(10) Patent No.: US 11,408,835 B2
(45) Date of Patent: Aug. 9, 2022

(54) MICROWAVE SOIL MOISTURE SENSOR BASED ON PHASE SHIFT METHOD AND INDEPENDENT OF ELECTRICAL CONDUCTIVITY OF THE SOIL

(71) Applicant: BioSense Institute—Research and Development Institute For Information Technologies in Biosystems, Novi Sad (RS)

(72) Inventor: Goran Kitic, Novi Sad (RS)

(73) Assignee: Biosense Institute-Research And Development Institute For Information Technologies In Biosystems, Novi Sad (RS)

( * ) Notice: Subject to any disclaimer, the term of this patent is extended or adjusted under 35 U.S.C. 154(b) by 60 days.

(21) Appl. No.: 16/975,674

(22) PCT Filed: Feb. 26, 2019

(86) PCT No.: PCT/RS2019/000010
§ 371 (c)(1),
(2) Date: Aug. 25, 2020

(87) PCT Pub. No.: WO2019/168423
PCT Pub. Date: Sep. 6, 2019

(65) Prior Publication Data
US 2021/0003514 A1    Jan. 7, 2021

(30) Foreign Application Priority Data
Feb. 27, 2018  (RS) .................................. P-20180253

(51) Int. Cl.
*G01N 22/04*     (2006.01)
*G01N 33/24*     (2006.01)

(52) U.S. Cl.
CPC ........... *G01N 22/04* (2013.01); *G01N 33/246* (2013.01)

(58) Field of Classification Search
CPC ............................. G01N 22/04; G01N 33/246
(Continued)

(56) References Cited
U.S. PATENT DOCUMENTS 7,135,871 B1 * 11/2006 Pelletier ................. G01N 22/04
324/640
7,239,150 B2 * 7/2007 Troxler .................. G01N 33/42
324/643
(Continued)

FOREIGN PATENT DOCUMENTS

WO    2006064266 A1    6/2006
WO    2012175976 A1    12/2012

*Primary Examiner* — Giovanni Astacio-Oquendo
(74) *Attorney, Agent, or Firm* — The Watson IP Group, PLC; Jovan N. Jovanovic

(57) ABSTRACT

The present invention relates to soil moisture and soil matric potential measurement using microwave sensor composed of sensor element (1), porous matrix (2), phase shift measurement circuit (3) and circuit protective layer (4). Operating principle is based on the phase shift method in which phase shift of the signal propagating along sensor element (1) is related to the porous matrix (2) moisture content. Porous matrix (2) is in contact with surrounding soil (5) and reflects its water content. Phase shift measurement circuit (3) excite sensor element (1) and measures phase shift. The sensor is independent of soil electrical conductivity owing to the operating frequency in microwave range (~GHz). In this manner, it is less sensitive to the soil type and therefore less demanding for calibration. The sensor is made of durable elements without consumable parts which enable a long-term operation. Its low power consumption makes it suitable for Internet of Things concept and automatic irrigation systems.

5 Claims, 3 Drawing Sheets

(58) Field of Classification Search
USPC .................... 324/640, 639, 637, 629, 600
See application file for complete search history.

(56) References Cited

U.S. PATENT DOCUMENTS

| | | | |
|---|---|---|---|
| 8,841,923 B1* | 9/2014 | Vanwiggeren | G01R 27/32 |
| | | | 324/606 |
| 2013/0131875 A1 | 5/2013 | Viera et al. | |
| 2021/0270754 A1* | 9/2021 | Wolleben | G01N 33/246 |
| 2021/0337721 A1* | 11/2021 | Zhao | G05B 19/4155 |
| 2022/0035366 A1* | 2/2022 | Canyon | G01N 22/04 |

* cited by examiner

MICROWAVE SOIL MOISTURE SENSOR BASED ON PHASE SHIFT METHOD AND INDEPENDENT OF ELECTRICAL CONDUCTIVITY OF THE SOIL

TECHNICAL FIELD

The present invention relates to sensors for determination of soil water content, and more particularly, to soil moisture determination by means of microwaves and changes in the dielectric constant of the material.

BACKGROUND ART

Exact measurement of soil moisture is needed in a variety of applications. In agriculture, proper growth, development, and maintenance of the plants significantly depend on soil water content. In the past, numerous sensors based on indirect methods for soil moisture measurement, were developed including electric conductivity method, dielectric permittivity method, tensiometric method and so on.

An example of the sensor solution based on the measurement of electrical conductivity, are electric resistance sensors. Electrical conductivity of the soil is measured between the electrodes placed directly in the soil. Consequently, the resistivity of the medium, which is in direct contact with electrodes on one side and surrounding soil on the other side, can be measured.

The device consists of a porous block made of gypsum or fiberglass in which two electrodes are placed as described in "Measurement of soil moisture using gypsum blocks" by B. Hanson et al.

When the device is buried in the soil, water moves from the area of lower matric potential to the area of higher matric potential which leads to the equilibrium of potentials between gypsum block and surrounding soil. When equilibrium of moisture is accomplished, the electric conductivity (resistivity) is measured by alternating current in order to eliminate the influence of the ion accumulation on the electrodes.

The main disadvantage of this type of sensors is the fact that conductivity of the soil is not exclusively related to the soil moisture, but also to the concentration of the ions in the soil. Therefore, it is practically impossible to eliminate this influence. The stated issue is substantially diminished when gypsum block sensors are used, since they saturate water from the soil by ions and in this way cancel the influence of the soil conductivity. However, resolving the problem of variable soil conductivity has generated another issue, since the gypsum block dissolves over time and the contact with surrounding soil is lost, which ultimately lowers the quality of measurements. Moreover, the measurement method is limited in terms of electrical conductivity to values higher than 6 dS/m. In order to overcome the issue of the contact, granular matrix or transfer matrix sensors have been invented. The matrix is usually made of quartz sand of high purity. An example of the sensor that uses this type of medium is described in the U.S. Pat. No. 5,179,347.

Although the stated approach has eliminated the issue of the poor contact between the sensor and soil, the other disadvantages of the previous solution remained—including depletion of gypsum tablet, long response time, temperature dependence, and inapplicability of the sensor in swelling soil.

Unlike the solution with gypsum tablet, the present invention does not contain any consumable parts as in the case of previously described gypsum tablet, which enables its long-lasting operation without performance degradation. Furthermore, the present invention is based on the measurement of dielectric permittivity, which has better temperature stability in comparison to electrical conductivity.

The most common sensors that rely on permittivity measurements are time-domain sensors, as well as capacitive and electrical impedance sensors. Their operating principle relies on the fact that water substantially changes relative permittivity of the soil since its dielectric constant is 78, which is significantly higher than the relative permittivity of air and minerals in the soil.

This change influences the propagation velocity of electromagnetic wave in the dielectric and therefore the time delay of the signal. This fact is used in time-domain soil moisture sensors such as time domain reflectometry (TDR) and time domain transmission (TDT) sensors. TDR sensors measure the time delay of the pulse that reflects from the properly terminated end of the sensor's waveguide. In general, TDR sensor is fabricated in the form of a waveguide made of two or three conductive rods which are placed in the soil with minimal disturbance, as explained in the U.S. Pat. No. 5,376,888. The result of measurement represents the average value of the permittivity along the sensor waveguide length. The precision of the reflectometric methods is limited by multiple reflection phenomena caused by soil inhomogeneity.

Unlike common reflectometry methods, accuracy of transmission time domain method is not influenced by multiple reflection, since the first detected pulse contains required information, as explained in the paper "A time domain transmission measurement system for dielectric characterizations" by B. Will et al. However, sensors based on transmission method require two ports, which creates additional challenges in sensor design in a way that both ports are placed in the soil.

Both TDR and TDT methods suffer from the influence of soil electrical conductivity on the attenuation of the measurement signal, which is not the case in the present invention since it is not dependent on soil electrical conductivity. Also, time domain methods are considerably more sensitive to noise when compared to the measurement of the phase of electrical signal, which is the underlying principle of the present invention.

In the case of capacitive sensors, the soil itself is employed as a dielectric medium of the capacitor (probe), whilst capacitor conductors are realized as two electrodes. The change of moisture content directly affects the total capacitance of the probe. The relative permittivity of soil can be determined based on the time needed to charge the capacitor or by using variable frequency oscillators to determine the resonant frequency of the circuit that includes the probe. The shape of electrodes is designed to enable a simple placement of the sensor into the soil, and thus the shape of electrodes is in the form of rods or plates as described in the patent US20100277185. Also, there are electrodes like the ones used in neutron scattering methods in the form of polyvinyl chloride pipes with metal ring pairs that form capacitors whose fringe capacitance changes with the change of soil moisture content, see U.S. Pat. No. 5,418,466.

Capacitive sensors are highly influenced by the soil type and therefore demand calibration. In the case of present invention, the influence of electrical conductivity, which is closely related to the soil type, can be practically avoided if operating frequency is cautiously selected which will be elaborated in detail later in the text. In this way, a solution that is more immune to the soil type which does not require calibration is obtained.

Another way to measure dielectric permittivity and therefore moisture content in the soil, is the measurement of the electrical impedance of an open waveguide, which is in direct contact with a soil sample. Open waveguide that is used for the measurement, is usually called probe or sensor and in most cases is realized in the form of coaxial line, which enables measurement in a wide frequency range. The probe is placed so that its open end is in contact with the sample, which provides the soil moisture, which changes the soil complex permittivity. In this way soil moisture of the sample influences the impedance "seen" by coaxial line at its end. In laboratory, measurements of the impedance are performed by reflection coefficient measurements with the help of vector network analyzer (VNA). In order to extract complex permittivity, the results of the measurements need to be compared to appropriate equivalent circuit. This additional step in the determination of soil moisture content is not needed in the case of present invention since it features all the supporting electronics for soil moisture measurement in the field.

The main disadvantage of impedance sensors is the requirement for expensive equipment such as VNA or impedance analyzer, which limits their use to laboratory conditions. For the purpose of the in-field applications, a wide frequency range was eliminated and measurements are made at a single frequency which is usually 100 MHz as explained in "Measurement of Soil Water Content Using a Simplified Impedance Measuring Technique" by G. J. Gaskin and J. D. Miller. The sensor, or more precisely waveguide used for in situ measurements is not of coaxial type, but it is realized as two or three conductive rods, as in the case of TDR probes, in order to facilitate placement in the soil. However, the proposed sensor is dependent on the type of the soil and demands calibration before usage since the frequency is relatively low. The present invention operates at sufficiently high frequency (~GHz), which practically eliminates the influence of the electrical conductivity which is closely related to soil type. In this manner, the need for calibration can be practically avoided.

One of the traditionally used solutions for soil measuring available water in the soil are tensiometers, a sensor solution that relies on tensiometric methods that measure soil matric potential (soil moisture tension). In the U.S. Pat. No. 4,068,525, the tensiometers that are composed of sealed plastic pipes are described. The pipes are filled with water, and on their bottoms a porous medium is placed, whilst on the opposite side a pressure gauge is mounted. The porous material is in contact with surrounding soil and provides water release from the pipe in the case of lower matric potential in the soil, or water absorption in the opposite case. In this manner, it is ensured that these two mediums are in the state of hydrodynamic equilibrium. The change in the water level in the pipe is related to the pressure gauge by which soil moisture tension of the soil is determined, with accuracy in the range of 0.1-1.0 kPa.

Owing to the operating principle, tensiometers can estimate the quantity of the water that is available to the plants. Furthermore, they are independent of soil salinity, since dissolved salts can freely move through porous medium thus minimizing the influence of the soil type. Also, it is possible to avoid usage of supporting electronics and power supply which, when combined with robust design, provides a long-lasting and independent sensor.

However, this type of sensor has disadvantage caused by the formation of gaps between porous medium and surrounding soil that dries, which enables entering of air into the porous material, therefore dynamic range of the tensiometer is from 0 to −85 kPa. Hence, tensiometers are not suitable for the swelling soil. The present invention is not limited by the above mentioned issues since it is based on permittivity measurements which do not require communicating vessels system. Moreover, tensiometers have to be protected from the frost since they are filled with water, therefore operating temperature range is from 0 to 80° C., which is not the case for the present invention which can operate in the temperature range from −40 to 85° C.

DISCLOSURE OF INVENTION

The main advantages of the present invention originate from its operating principle based on the phase shift method and optimal operating frequency. Since the phase shift method measures phase and not the amplitude of the signal, the measurement results are more immune to the noise. By choosing optimal operating frequency in the microwave range (~GHz) it is possible to neglect the influence of soil electrical conductivity. In this manner, it is achieved that the sensor is more independent from soil type in comparison to the state-of-the-art solutions and the need for its calibration is reduced. The sensor is made of robust parts without consumable components, which enables its long-lasting operation with performances stable over time. Supporting electronics enables economical operation suitable for Internet of Things (IoT) concept, integration in wireless sensors networks as well as in systems for automatic irrigation. The porous matrix within the sensor maintains hydrodynamic equilibrium with surrounding soil, thereby conveying a realistic state of the moisture content to the sensor element, and, at the same time, enabling excellent contact with the sensor element. By introduction of the relation between retention curve of the porous matrix and sensor output, it is possible the measure soil matric potential of the soil as well, which represents the best indicator of the water available to the plants.

BEST MODE FOR CARRYING OUT OF THE INVENTION

Before disclosing the details of the invention, it is important to understand and stress that the present invention is not limited to the details of the construction illustrated and described below. The terms used in the description of the invention serve to understand the invention, and not for its limitations.

Figure 1:
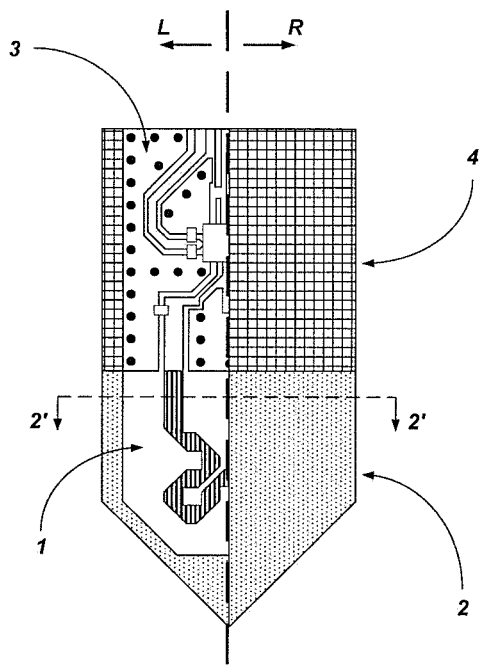
FIG. 1—shows a simplified view of the invention together with its inner structure FIG. 2—shows a cross section 2'-2' on FIG. 1 of the invention at the position of sensor element and porous matrix 2
Figure 2:
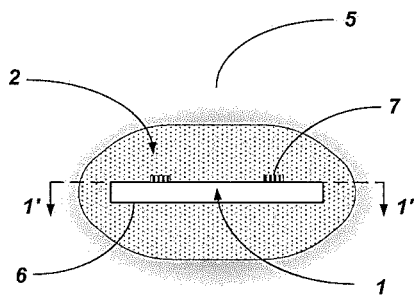

An example of the realization of the soil moisture sensor is shown in FIG. 1. The side marked with L is the cross-section of the sensor defined in FIG. 2 by 1'-1', while side R is the exterior of the sensor. The basic components of the sensor are the sensor element 1, which is in direct contact with the porous matrix 2, phase shift measurement circuit 3, and the protective layer of the electronic circuit 4. The operating principle of the sensor and its components will be described in detail below.

The operating principle of the sensor is based on the phase shift method. The advantage of this method lays in the fact that phase measurement is less susceptible to noise, than amplitude measurements, which is the case in time domain solutions. Furthermore, the sensor performs measurements at one operating frequency, which simplifies the realization of the supporting electronics, and lowers the price of the sensor. Finally, the electronic circuit, which supports the method, is low power and as such suitable for integration into IoT systems.

The phase shift method measures the phase shift of a sinusoidal signal propagating along the sensor element 1 realized as a waveguide. The phase shift θφ is determined by the velocity and frequency of the signal as well as by the physical properties of the sensor element 1 and the porous matrix 2 surrounding it:

$$\Delta\varphi = \frac{\omega L_{SE}}{v_p},$$

where ω is angular frequency, $v_p$ is the phase velocity of the signal, and $L_{SE}$ is the length of the sensor element 1.

The phase velocity of the signal depends on the dielectric permittivity of the porous matrix 2. The porous matrix 2 is in direct contact with surrounding soil 5 and its dielectric permittivity is directly affected by the soil moisture content. The phase velocity can be calculated as:

$$v_p = \frac{\sqrt{2}}{\sqrt{\mu\varepsilon}} \frac{1}{\sqrt{1+\sqrt{1+\frac{\sigma^2}{\omega^2\varepsilon^2}}}},$$

where μ, ε, and σ are the real parts of the permeability, permittivity, and electrical conductivity of the medium through which the signal is propagating, respectively. The main advantage of the phase-shift method lies in the fact that at the sufficiently high frequencies (~GHz), the influence of conductivity can be neglected. The electrical conductivity of the soil is closely related to the type of soil and it is determined by its texture, level of organic matter and soil salinity, as shown in "Precision farming tools: Soil electrical conductivity" by R. B. Grisso et al. In this manner, it is ensured that the sensor is immune to the type of soil whose moisture content is measured.

At sufficiently high frequencies, the condition $\sigma^2/(\omega E)^2 \ll 1$ is met, and the expression for the phase velocity can be reduced to:

$$v_p = \frac{1}{\sqrt{\mu\varepsilon}}.$$

Therefore, the phase velocity is determined only by permittivity and permeability, where the latter does not change with the soil moisture content.

The waveguide of the sensor is the sensor element 1 which can be realized in the form of planar lines such as microstrip lines, coplanar waveguides, slotline or similar. These planar lines are realized by the technology of printed boards that is common in the electronics industry and can be easily integrated with supporting electronics. Planar lines can be realized on substrates 6 based on Teflon specially designed for the microwave circuits fabrication, or on ceramic substrates based on an alumina or conventional FR-4 substrates or similar. The sensor element 1 can be protected against adverse environment conditions by layer based on polyurethane, acrylate or similar. The conductive parts 7 of the sensor element may and may not be made of carbon materials or be protected by gold.

The influence of soil moisture on the propagation of the signal is incorporated in the effective permittivity of the sensor element 1, which depends on the dielectric constants of the surrounding environment, the porous matrix 2, and the substrate 6 of the sensor element 1. For instance, the effective permittivity of the microstrip line can be calculated using the equation $$\varepsilon_{\text{eff}} = \frac{\varepsilon_s + \varepsilon_{pm}}{2} + \frac{\varepsilon_s - \varepsilon_{pm}}{2}\frac{1}{\sqrt{1+12\frac{h}{w}}},$$

where $\varepsilon_s$ and $\varepsilon_{pm}$ are the permittivity of dielectric substrate 6 and the porous matrix 2, respectively, h is the height of the substrate, and w is the width of the microstrip line.

The porous matrix 2 provides a good contact with the sensor element 1 and the surrounding soil 5 with which it is in the state of hydrodynamic equilibrium, therefore convey a realistic state of the soil moisture content to the sensor element 1. The correlation of the porous matrix 2, the sensor element 1, and the surrounding soil 5 can be clearly seen in FIG. 2, which represents the cross section indicated by 2'-2' in FIG. 1. The porous matrix 2 can be realized by commercially available materials such as quartz flour, phenol foam, clay, zeolite or similar. Newly developed materials based on mixtures of microspheres of different sizes to mimic the texture of the soil can be used. Microspheres can be made of glass, polyethylene, polymethyl methacrylate or similar. Matrix 2 can be based on a mixture of clay and polyethylene glycol or epoxy resin, or similar, which enables control of the porosity of the matrix 2. The porous matrix 2 may or may not be placed in a perforated housing that allows the undisturbed movement of water from the soil 5 into the matrix 2 and vice versa and, on the other hand, provides the mechanical strength of the matrix 2 itself. The size of pores and particles of the matrix 2 is designed in a manner to cover the range of interest of matric potentials for plants, starting from field capacity (−33 kPa), over lento-capillary point (−625 kPa) as the lower limit of optimal soil moisture content, ending with the wilting point (−1500 kPa).

Figure 3:
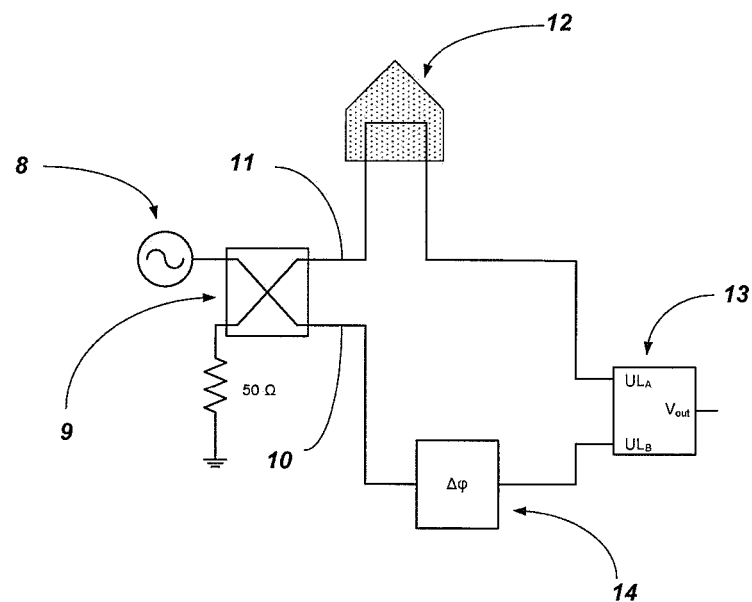
FIG. 3—shows a block diagram of phase shift measurement circuit 3

The block diagram of the phase shift measurement circuit 3 is shown in the FIG. 3. Operating principle of the circuit is the following:

Sinusoidal 2.2 GHz signal generated by the source 8, that is, microwave oscillator, is divided by the quadrature hybrid 9 into referent signal 10 and measurement signal 11. The measurement signal 11 propagates along sensor element 1 where phase shift occurs according to the dielectric properties of the surrounding porous matrix 2. Sensor element 1 and porous matrix 2 form sensor probe 12. The signal from the sensor probe 12 is fed into the input of the phase detector 13 which compares the phase of the measurement 11 and the referent signal 10. The output of the phase detector 13 is the voltage output proportional to the phase shift of the input signals which is related to the moisture content. Referent signal 10 propagates through the phase-shifter module 14 which has the purpose to provide the calibration of the sensor and to overcome deviations of the nominal properties of the materials and components used for sensor fabrication. In this manner, the repeatability of measurement of the different sensor will be secured.

Figure 4:
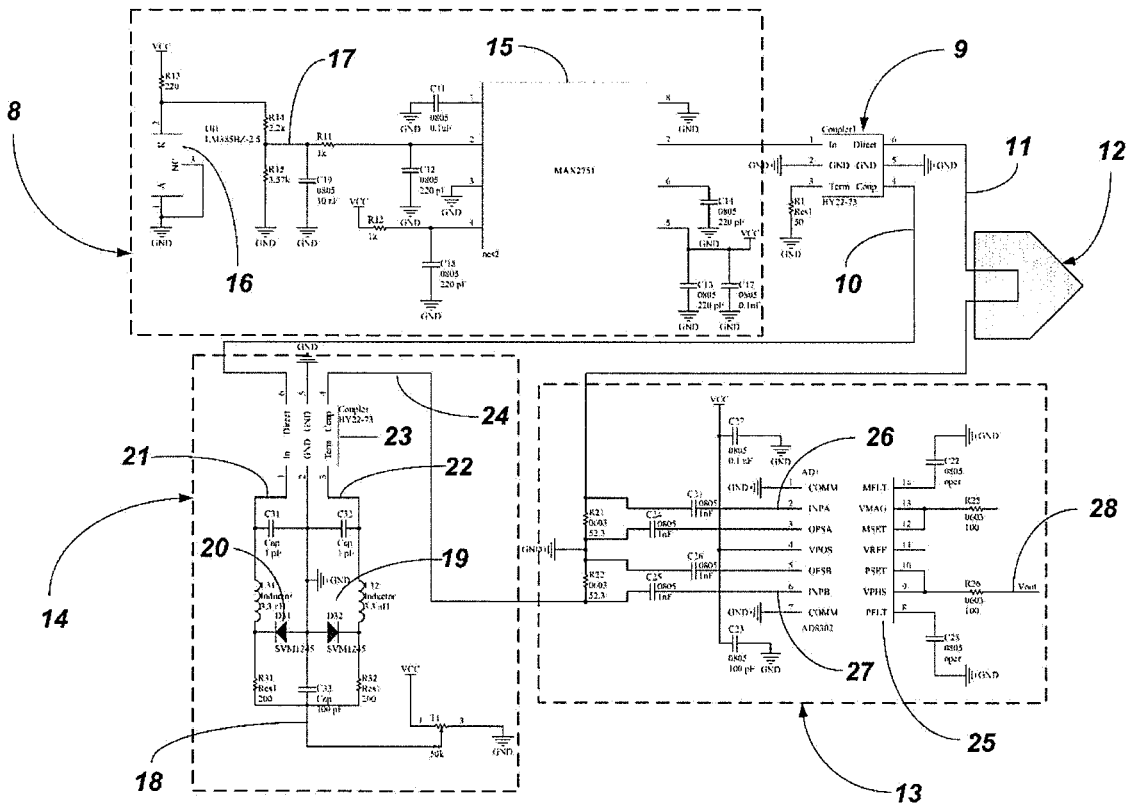
FIG. 4—shows a circuit drawing of phase shift measurement circuit 3

The circuit drawing of phase shift measurement circuit 3 is shown in FIG. 4, which also depicts the previously described block diagram shown in FIG. 3. The oscillator is realized as the voltage-controlled oscillator MAX2751 15, which is adjusted by voltage reference 16 and the voltage divider 17 to the operating frequency of 2.2 GHz. The signal from the oscillator 15 is divided into measurement 11 and referent signal 10 by a quadrature coupler 9 realized by commercially available couplers HY22-73 or C2023J5003AHF or similar one, that are able to divide the signal at the operating frequency. The phase shifter module 14 performs a voltage-controlled phase shift, which fine-tunes the difference in the phase between the measurement signal 11 and the reference signal 10. The phase shift is achieved by changing the control voltage 18 that affects the capacitance of the varactor diodes 19 and 20. The change in capacitance affects the signals 21 and 22 which superimpose with the input reference signal 10 through a quadrature coupler 23 and thereby modify its phase at the output of module 24. For a detailed description of the operation, refer to "A varactor conferred phase shifter for PCS base station application" by Skyworks. Measurement of the phase difference between the measuring signal 11 and the reference signal 10 is carried out by the phase detector module 13 realized with the integrated circuit AD8302 Analogue Devices 25, which is adjusted according to the manufacturer's recommendation for the measurement of the phase difference of the signals at its inputs 26 and 27. The integrated circuit AD8302 25 on its output 28 provides a voltage signal that is proportional to the phase difference of the signal at its inputs. In order to prevent short circuits of the phase shift measurement circuit 3, a protective layer 4 is applied in the form of a waterproof material such as silicone, acrylate, polyurethane or an appropriate epoxy resin.

Figure 5:
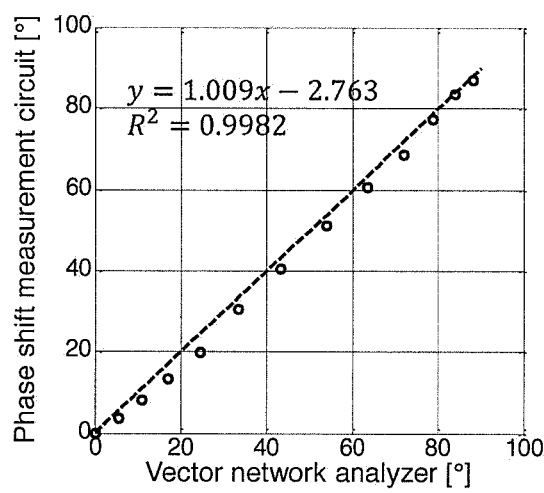
FIG. 5—compares phase shift measurement circuit 3 to the vector network analyzer as a reference device FIG. 6—demonstrates independence of the invention from the electrical conductivity of the soil owing to the sufficiently high operating frequency FIG. 7—shows soil moisture measurement results obtained from the present invention

The phase shift measurement circuit 3 was experimentally confirmed by comparing the results of the phase shift measurement in the range 0-90 with the results obtained using VNA as the referent device. The comparison of the two results is shown in FIG. 5.

Based on the described method and sensor components, the operating principle of the sensor can be explained, which comprises the following:
1) Increased moisture content of the surrounding soil 5 increases the permittivity of the porous matrix 2.
2) The increase in the permittivity of the porous matrix 2 also increases the effective permittivity of the sensor element 1.
3) The phase velocity of the signal $v_p$ decreases.
4) The phase shift of the signal $\Delta \varphi$ increases, thereby changing the voltage at the output of the phase shift measurement circuit 28.

Based on the operating principle, it can be concluded that certain soil moisture contents correspond to certain phase shifts of signals or output voltages 28, which is a necessary condition for constructing a calibration curve that relates the phase shift of the signal to the amount of water in the soil. The present invention may determine the matric potential of the soil by relating the retention curve of the porous matrix that relates the water content to a matric potential, to the corresponding phase shift that the sensor detects. In this manner, the sensor can measure soil moisture tension, thus representing a hybrid solution of the tensiometer and soil moisture sensor based on permittivity measurement. The sensor retains the advantages of both solutions in terms of independence of the soil type, response time, robustness, and compatibility options with the IoT concept.

Figure 6:
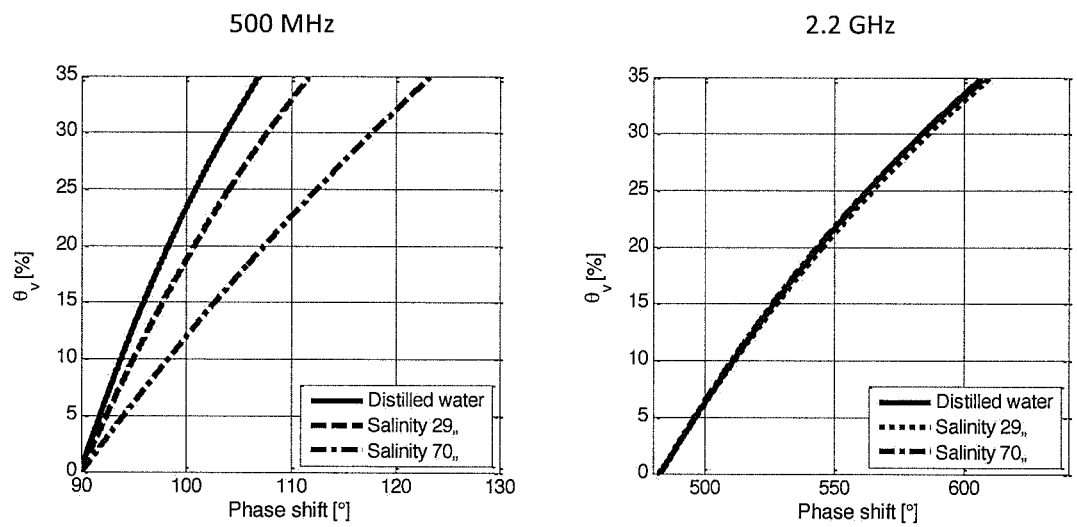
Figure 7:
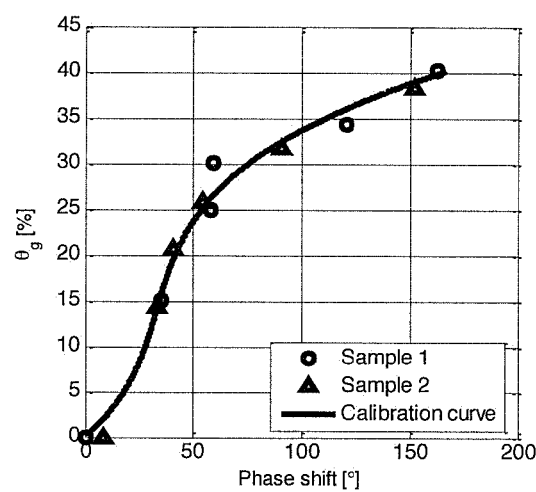

As previously mentioned, the main advantage of the sufficiently high operating frequency in combination with phase shift method is that it enables the measurement of soil moisture that it is not influenced by the electrical conductivity of the soil, that is closely related to the soil type. This statement was experimentally confirmed. The calibration curves for quartz sand wetted with distilled water and water of two different salinity levels (electrical conductance) of 29% and 70%, are shown in FIG. 6, at the frequencies of 500 MHz and 2.2 GHz. As it can be seen, there is a significant difference in the calibration curves of the different treated samples at the frequency of 500 MHz. However, if the operating frequency is increased to 2.2 GHz, the calibration curves for all three cases coincide.

The present invention was tested under real conditions by measuring the moisture content of two different soil samples. The results of the agrochemical analysis of the samples are shown in Table 1.

TABLE 1

| Sample | pH in KCl | pH in H$_2$O | Humus [%] | Total N [%] | Al—P$_2$O$_5$ [mg/100 g] | Al—K$_2$O [mg/100 g] |
|---|---|---|---|---|---|---|
| 1 | 7.25 | 8.29 | 3.39 | 0.17 | 17.92 | 28.53 |
| 2 | 7.30 | 8.27 | 2.05 | 0.10 | 13.69 | 21.70 |

Series of phase shifts measurements with the sensor were performed for both samples. Soil moisture levels were ranging from the field capacity to a completely dry sample. Based on the measurement results of sample 1, a calibration curve had been constructed, and afterwards used to determine the moisture content of the sample 2. The values of the moisture content obtained by the calibration curve, were in accordance with the actual moisture content, which is confirmed by the absolute error lower than 0.01 g/g. This illustrates the independence of the sensor operation from the soil type.

INDUSTRIAL APPLICABILITY

According to the Food and Agriculture Organization of the United Nations, optimal usage of irrigation systems can increase yields by an average of 79%. The proposed solution of soil moisture sensors would contribute to the improvement of such systems and increase yields through their performance. The sensor would be placed in the soil at the root level. In the future, sensors could be placed at several depths to monitor the water dynamics in the soil. On the other hand, a developed sensor could also be used for the purpose of ground truth measurements in combination with remote systems that measure moisture content over large areas using satellite images or Synthetic Aperture radars.

Owing to its low power consumption, the sensor can be included into IoT concept that keeps up with the Fourth Industrial Revolution.

The invention claimed is:

1. A microwave soil moisture sensor to implement a phase shift that is independent of an electrical conductivity of a soil, the microwave soil moisture sensor comprising:
  a sensor element with a protective layer;
  a porous matrix that surrounds the sensor element and is in direct contact with the sensor element; and
  a phase shift measurement circuit covered with a protective layer.

2. The microwave soil moisture sensor according to claim 1, wherein sensor element is realized in a form of planar waveguide, and is protected from an aggressive environment with a polyurethane based layer.

3. The microwave soil moisture sensor according to claim 1, wherein the porous matrix provides a complete contact with the sensor element and a surrounding soil, and, at a same time, is in a state of hydrodynamic equilibrium with the surrounding soil.

4. The microwave soil moisture sensor according to claim 3, wherein the porous matrix includes morphological properties that cover soil matric potentials starting from a field capacity (−33 kPa), over a lento-capillary point (−625 kPa), to a wilting point (−1500 kPa) and, at the same time, is mechanically stable and robust.

5. The microwave soil moisture sensor according to claim 1, wherein the phase shift measurement circuit is comprised of a microwave oscillator, connected to a quadrature hybrid, which is connected to the sensor element and a phase-shifter module by a measurement and referent signal, respectively, further, the sensor element and the phase-shifter module are connected to inputs of a phase detector module whose output voltage is related to a moisture content and a soil matric potential of the soil.

* * * * *